(12) United States Patent
Takasugi et al.

(10) Patent No.: US 8,980,337 B2
(45) Date of Patent: Mar. 17, 2015

(54) TABLET COMPOSITION CONTAINING KAMPO EXTRACT

(75) Inventors: Yasuhiro Takasugi, Ibaraki (JP); Kazuhiro Matsumoto, Ibaraki (JP)

(73) Assignee: Tsumura & Co., Tokyo (JP)

( * ) Notice: Subject to any disclaimer, the term of this patent is extended or adjusted under 35 U.S.C. 154(b) by 500 days.

(21) Appl. No.: 12/306,676

(22) PCT Filed: Jun. 21, 2007

(86) PCT No.: PCT/JP2007/062515
§ 371 (c)(1), (2), (4) Date: Feb. 17, 2009

(87) PCT Pub. No.: WO2008/001672
PCT Pub. Date: Jan. 3, 2008

(65) Prior Publication Data
US 2009/0181112 A1 Jul. 16, 2009

(30) Foreign Application Priority Data
Jun. 29, 2006 (JP) .................................. 2006-179341

(51) Int. Cl.
*A61K 36/00* (2006.01)
*A61K 9/20* (2006.01)
*A61K 47/02* (2006.01)
*A61K 47/38* (2006.01)

(52) U.S. Cl.
CPC ............. *A61K 9/2009* (2013.01); *A61K 9/2027* (2013.01); *A61K 9/2054* (2013.01); *A61K 9/2059* (2013.01); *A61K 36/00* (2013.01); *A61K 47/02* (2013.01); *A61K 47/38* (2013.01)
USPC ........................................................ 424/725

(58) Field of Classification Search
None
See application file for complete search history.

(56) References Cited

U.S. PATENT DOCUMENTS

| 6,413,546 B1 * | 7/2002 | He et al. ........................ 424/464 |
| 7,374,784 B2 | 5/2008 | Kroll et al. |
| 2004/0067265 A1 * | 4/2004 | Kroll et al. .................... 424/730 |

FOREIGN PATENT DOCUMENTS

| EP | 1541161 A1 * | 6/2005 |
| JP | 01-258625 A | 10/1989 |
| JP | 2005-502729 A | 1/2005 |
| WO | 2004/006945 A1 | 1/2004 |

OTHER PUBLICATIONS

Koshikawa et al, Effects of Hochu-ekki-to, Yoku-kan-san and Saiko-ka-ryukotsu-borei-to on behavioral despair and acetic acid-induced writhing in mice, Methods and Findings in Experimental and Clinical Pharmacology (1998), 20(1), 47-51.*
Masayuki Kakizawa, "Closcarmellose Sodium Kiccolate ND-2HS, ND-200 no Goshokai", Dai 21 Kai Seizai to Ryushi Sekkei Shinopojiumu Koen Yoshishu, 2004, pp. 33 to 36, p. 33, 1. Hajimeni.
Eiji Kawahata, "Evaluation on Collapse Agency in Simply Manufacturing Orally Disintegrating Tablet", Annual Report of Toyama Prefectural Institute for Pharmaceutical Research, 2005, pp. 41-44, p. 42, tables 2, 6.
Maya Tagawa, et al. "Effect of Various Disintegrants on Drug Release Behavior from Tablets", Journal of Pharmaceutical Science and Technology, Japan, 2003, vol. 63, No. 4, pp. 238-248, p. 244, Fig. 8.
International Search Report for PCT/JP2007/062515 dated Jul. 30, 2007.
Communication dated Nov. 27, 2012 issued in Japanese Patent Application No. 2008-522513.

* cited by examiner

*Primary Examiner* — Qiuwen Mi
(74) *Attorney, Agent, or Firm* — Sughrue Mion, PLLC (57) ABSTRACT

Provided is a tablet composition containing Kampo extract having more excellent disintegration and dissolution properties than ever before. The tablet composition containing Kampo extract contains a Kampo extract powder, croscarmellose sodium, and sodium hydrogen carbonate. The Kampo extract powder is preferably at least one extract powder selected from the group consisting of Kakkonto, Kakkontokasenkyushin'i, Shoseiryuto, Tokishakuyakusan, Kamishoyosan, Keishibukuryogan, Hochuekkito, Bofutushosan, Goshajinkigan, Maobushisaishinto, Keishikajutsubuto, Juzentaihoto, Sokeikakketsuto, Shakuyakukanzoto, Keishininjinto, Tokakujokito, Yokukansan, Goreisan, and Eppikajutsuto.

9 Claims, 3 Drawing Sheets

FIG.8 ered to as "tablet composition"), and in detail relates to a
TABLET COMPOSITION CONTAINING KAMPO EXTRACT

TECHNICAL FIELD

The present invention relates to a tablet composition containing Kampo extract (hereinafter, occasionally, simply referred to as "tablet composition"), and in detail relates to a tablet composition containing Kampo extract being excellent in disintegration and dissolution properties.

BACKGROUND ART

A Kampo extract powder (hereinafter, occasionally referred to as "extract powder") is obtained by extracting a Kampo formula with an aqueous solvent followed by concentration and drying. Therefore, in general, the powder is highly hygroscopic and is thereby desired to be prepared by a process not requiring the addition of water. Such a preparation process is also preferred because it allows omission of the granulation step and ensures stability for those that are unstable to water.

Accordingly, employed are a direct tableting method where tablets are prepared by direct compression of a powder mixture of a tablet composition containing an extract powder and a dry tableting method (slug method) where tablets are prepared by forming a granulated substance having a small diameter and containing an extract powder and tableting a powder mixture of a tablet composition containing the granulated substance.

However, such Kampo extract-containing tablets produced by these tableting methods have a long disintegration time, which cannot be sufficiently improved only by adding a general disintegrant, and have low dissolution properties. Thus, satisfactory tablets have not been prepared.

In order to solve this problem, some methods have been tried. For example, the content of an extract powder in a tablet is decreased, or a large amount of a diluent, a disintegrant, a binder, or other excipients are added to a tablet. However, these methods cause problems, for example, an increase in dose of tablets, an increase in tablet size, and an increase in manufacturing cost due to the expensive disintegrant. Furthermore, a tablet of which dissolution properties are improved by adding sodium hydrogen carbonate is also known, but it is not imparted with sufficient advantageous effect.

In addition, if a composition contains a large amount of sodium hydrogen carbonate, it is concerned that the alkalinity of the sodium hydrogen carbonate may affect the stability of the extract powder.

As a technology for solving the above-mentioned problems and improving the disintegration and dissolution properties of tablets containing a Kampo extract powder, the present applicant has already proposed a tablet composition containing Kampo extract that contains a Kampo extract powder, cellulose glycolic acid, and sodium hydrogen carbonate (Patent Document 1).

Patent Document 1: International Patent Publication No. WO2004/006945 (for example, Claims)

DISCLOSURE OF INVENTION

Problems to Be Solved by the Invention

Though the tablet composition containing Kampo extract described in Patent Document 1 is considerably improved in the disintegration and dissolution properties compared to those in the previous one, recently, further improvement is required. In addition, it is desired to decrease the amount of sodium hydrogen carbonate used.

Accordingly, it is an object of the present invention to provide a tablet composition containing Kampo extract having more excellent disintegration and dissolution properties than ever before.

Means for Solving the Problems

In order to achieve the object, the present inventors have conducted intensive studies and, as a result, have found that a tablet composition that can have more improved disintegration and dissolution properties than ever before, even in the case of that the amount of sodium hydrogen carbonate is decreased, can be obtained by blending a certain compound with a Kampo extract powder. Thus, the present invention has been completed.

That is, in order to solve the above-mentioned problems, the tablet composition containing Kampo extract of the present invention characteristically includes a Kampo extract powder, croscarmellose sodium, and sodium hydrogen carbonate.

Effect of the Invention

As described above, according to the present invention, it can be provided a tablet composition containing Kampo extract having excellent disintegration and dissolution properties, even in the case that the amount of sodium hydrogen carbonate is decreased, by blending a certain compound with a Kampo extract powder.

BEST MODES FOR CARRYING OUT THE INVENTION

Specific embodiments of the present invention will be described in detailed below.

The Kampo extract powder in the present invention is obtained by decocting a usual Kampo formula and concentrating and drying the decoction. Examples of the extract powder include, but are not limited to, Kakkonto, Kakkontokasenkyushin'i, Shoseiryuto, Tokishakuyakusan, Kamishoyosan, Keishibukuryogan, Hochuekkito, Bofutushosan, Goshajinkigan, Maobushisaishinto, Keishikajutsubuto, Juzentaihoto, Sokeikakketsuto, Shakuyakukanzoto, Keishininjinto, Tokakujokito, Yokukansan, Maoto, Goreisan, and Eppikajutsuto. In addition, crude drug extract powders that are each prepared by decocting one or more crude drugs and concentrating and drying the decoction are also included.

The amount of the Kampo extract powder in the tablet composition is preferably 40 to 80% by weight and more preferably 50 to 70% by weight. If the amount of the Kampo extract powder is less than this range, the dose (necessary amount of composition) per day is increased, which is undesirable. On the other hand, if the amount is higher than this range, the effects that improve disintegration and dissolution properties according to the present invention are not sufficiently achieved.

The croscarmellose sodium used in the present invention is commercially available. For example, croscarmellose sodium available under the trade name "Kiccolate ND-2HS", which is manufactured by Nichirin Chemical Industries, Ltd., can be preferably used.

The amount of croscarmellose sodium is preferably 5 to 30 parts by weight and more preferably 10 to 20 parts by weight based on 100 parts by weight of the Kampo extract powder. In particular, when the Kampo extract powder is an extract powder of Keishibukuryogan, the amount of croscarmellose sodium is preferably 8 to 20 parts by weight. If the amount of croscarmellose sodium is less than this range, the effects that improve disintegration and dissolution properties according to the present invention are not sufficiently achieved. On the other hand, if the amount is higher than this range, the tablets cannot be imparted with sufficient hardness.

The amount of sodium hydrogen carbonate is preferably 5 to 30 parts by weight and more preferably 10 to 20 parts by weight based on 100 parts by weight of the Kampo extract powder. In particular, when the Kampo extract powder is an extract powder of Keishibukuryogan, the amount of sodium hydrogen carbonate is preferably 8 to 20 parts by weight. If the amount of sodium hydrogen carbonate is less than this range, the effects that improve disintegration and dissolution properties according to the present invention are not sufficiently achieved. On the other hand, if the amount is higher than this range, hardness of tablets and stability of the Kampo extract powder are insufficient.

When the tablet composition of the present invention is prepared by direct powder tableting, a mixture is prepared by blending croscarmellose sodium and sodium hydrogen carbonate with a Kampo extract powder and further blending crystalline cellulose and other components therewith according to need, and the resulting mixture is compressed into tablets. The compression may be carried out by any method without particular limitation, and a common tableting machine can be used.

The tablet composition of the present invention may include a diluent, a binder, a fluidizer, a lubricant, and other excipients according to need. Examples of such excipients include sugars and sugar alcohols such as lactose, cornstarch, maltose, and mannitol; starches and starch derivatives such as maize starch, dextrin, and pregelatinized starches; celluloses and cellulose derivatives such as crystalline cellulose and hydroxypropyl cellulose; inorganic substances such as synthetic aluminum silicate, calcium phosphate, calcium hydrogen phosphate, talc, and light anhydrous silicic acid; and fatty acids such as magnesium stearate and calcium stearate.

EXAMPLES

The present invention will be described in detail with reference to Examples below. Hereinbelow, all "%" means "% by weight".

Examples 1-1, 1-2, and Comparative Examples 1-1 to 1-12

Powder mixtures for tableting were prepared according to formulae shown in the following tables 1 and 2 and were compressed using a tableting machine to obtain test tablets weighing 540 mg.

Then, the obtained test tablets were subjected to a disintegration test, which was carried out according to the disintegration test method described in the Japanese Pharmacopoeia. Purified water of 37° C. was used as a test liquid, and the time until the tablet is disintegrated was measured. Disintegration times of six tablets of each formula were measured, and the average thereof was calculated.

The test tablets were also subjected to a dissolution test, which was carried out according to the second method of dissolution test (Paddle method) described in the Japanese Pharmacopoeia under the following conditions:
Test liquid: purified water
Test liquid volume: 900 ml
Liquid temperature: 37° C.
Paddle rotation speed: 50 $min^{-1}$
Detector: UV (ultraviolet light)

Figure 1:
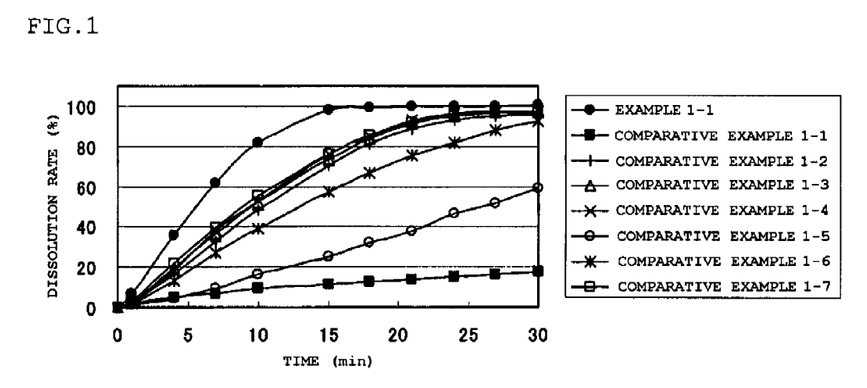
FIG. 1 shows dissolution curves of tablets prepared in Example 1 and Comparative Examples 1-1 to 1-7.
Figure 2:
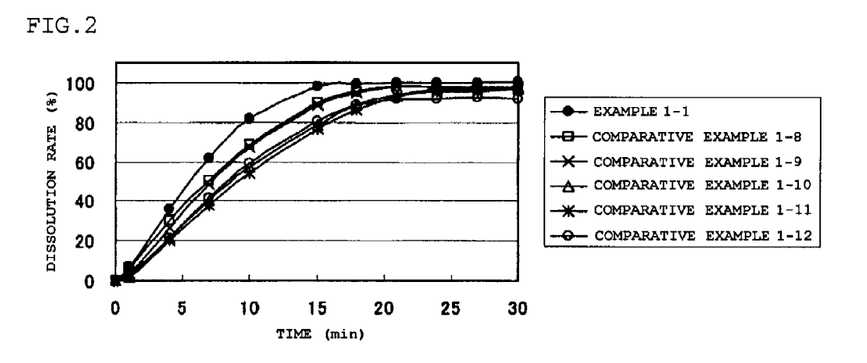
FIG. 2 shows dissolution curves of tablets in Example 1 and Comparative Examples 1-8 to 1-12.

The test results are also shown in the following tables 1 and 2. FIGS. 1 and 2 show dissolution curves in Examples 1-1 and Comparative Examples 1-1 to 1-7 and dissolution curves in Examples 1-1 and Comparative Examples 1-8 to 1-12, respectively, which were obtained by the same dissolution test conducted more concisely.

TABLE 1

| | | Example 1-1 | Example 1-2 | Comparative Example 1-1 | Comparative Example 1-2 | Comparative Example 1-3 | Comparative Example 1-4 | Comparative Example 1-5 | Comparative Example 1-6 | Comparative Example 1-7 |
|---|---|---|---|---|---|---|---|---|---|---|
| Formula (%) | Keishibukuryogan extract powder | 60.0 | 60.0 | 60.0 | 60.0 | 60.0 | 60.0 | 60.0 | 60.0 | 60.0 |
| | Sodium hydrogen carbonate | 5.0 | 10.0 | 0.0 | 5.0 | 10.0 | 15.0 | 0.0 | 0.0 | 0.0 |
| | Croscarmellose sodium | 5.0 | 10.0 | 0.0 | 0.0 | 0.0 | 0.0 | 5.0 | 10.0 | 15.0 |
| | Crystalline cellulose | 29.2 | 19.2 | 39.2 | 34.2 | 29.2 | 24.2 | 34.2 | 29.2 | 24.2 |
| | Light anhydrous silicic acid | 0.3 | 0.3 | 0.3 | 0.3 | 0.3 | 0.3 | 0.3 | 0.3 | 0.3 |
| | Magnesium stearate | 0.5 | 0.5 | 0.5 | 0.5 | 0.5 | 0.5 | 0.5 | 0.5 | 0.5 |
| | Total | 100.0 | 100.0 | 100.0 | 100.0 | 100.0 | 100.0 | 100.0 | 100.0 | 100.0 |
| | Disintegration time (min) | 13 | 13 | 74 | 29 | 23 | 17 | 36 | 18 | 23 |

TABLE 1-continued

|  |  | Example 1-1 | Example 1-2 | Comparative Example 1-1 | Comparative Example 1-2 | Comparative Example 1-3 | Comparative Example 1-4 | Comparative Example 1-5 | Comparative Example 1-6 | Comparative Example 1-7 |
|---|---|---|---|---|---|---|---|---|---|---|
| Dissolution rate | 5 min (%) | 45 | 48 | 6 | 22 | 25 | 25 | 6 | 18 | 28 |
|  | 10 min (%) | 82 | 85 | 9 | 48 | 52 | 53 | 16 | 39 | 55 |
|  | 15 min (%) | 98 | 101 | 11 | 70 | 74 | 76 | 25 | 57 | 76 |
|  | 30 min (%) | 101 | 104 | 18 | 95 | 97 | 98 | 59 | 92 | 97 |

TABLE 2

|  |  | Comparative Example 1-8 | Comparative Example 1-9 | Comparative Example 1-10 | Comparative Example 1-11 | Comparative Example 1-12 |
|---|---|---|---|---|---|---|
| Formula (%) | Keishibukuryogan extract powder | 60.0 | 60.0 | 60.0 | 60.0 | 60.0 |
|  | Sodium hydrogen carbonate | 5.0 | 5.0 | 5.0 | 5.0 | 5.0 |
| Disintegrant | Carmellose | 5.0 | — | — | — | — |
|  | Carmellose calcium | — | 5.0 | — | — | — |
|  | Carboxy starch sodium | — | — | 5.0 | — | — |
|  | Low-substituted hydroxypropyl cellulose | — | — | — | 5.0 | — |
|  | Kollidon CL | — | — | — | — | 5.0 |
|  | Crystalline cellulose | 29.2 | 29.2 | 29.2 | 29.2 | 29.2 |
|  | Light anhydrous silicic acid | 0.3 | 0.3 | 0.3 | 0.3 | 0.3 |
|  | Magnesium stearate | 0.5 | 0.5 | 0.5 | 0.5 | 0.5 |
|  | Total | 100.0 | 100.0 | 100.0 | 100.0 | 100.0 |
| Disintegration time (min) |  | 17 | 19 | 24 | 23 | 21 |
| Dissolution rate | 5 min (%) | 37 | 33 | 28 | 26 | 28 |
|  | 10 min (%) | 68 | 67 | 57 | 54 | 59 |
|  | 15 min (%) | 90 | 89 | 79 | 77 | 81 |
|  | 30 min (%) | 98 | 98 | 97 | 97 | 92 |

The results of the above tests confirmed that when tablets of a Keishibukuryogan extract powder contain a combination of 5% or 10% sodium hydrogen carbonate and croscarmellose sodium, the tablets disintegrate more rapidly than tablets containing them alone do and are also rapidly dissolved, and that when tablets of a Keishibukuryogan extract powder contain sodium hydrogen carbonate and croscarmellose sodium as disintegrants, the tablets have a shorter disintegration time and better dissolution properties than those of tablets containing other disintegrants.

Example 2 and Comparative Examples 2-1 to 2-3

Powder mixtures for tableting were prepared according to formulae shown in the following table 3 and were compressed using a tableting machine to obtain test tablets weighing 540 mg.

Then, the obtained test tablets were subjected to the disintegration test as in the above-mentioned Examples, and the hardness and the degree of abrasion of the tablets were measured.

The hardness of the tablets was measured with a Kiya type digital hardness meter, and the degree of abrasion was measured with a tablet friabilator.

TABLE 3

|  |  | Example 2 | Comparative Example 2-1 | Comparative Example 2-2 | Comparative Example 2-3 |
|---|---|---|---|---|---|
| Formula (%) | Keishibukuryogan extract powder | 60.0 | 60.0 | 60.0 | 60.0 |
|  | Sodium hydrogen carbonate | 5.0 | 5.0 | 5.0 | 5.0 |
| Disintegrant | Croscarmellose sodium | 5.0 | — | — | — |
|  | Carmellose | — | 5.0 | — | — |
|  | Kollidon CL | — | — | 5.0 | — |
|  | L-HPC | — | — | — | 5.0 |

TABLE 3-continued

|  | Example 2 | Comparative Example 2-1 | Comparative Example 2-2 | Comparative Example 2-3 |
|---|---|---|---|---|
| Crystalline cellulose | 29.2 | 29.2 | 29.2 | 29.2 |
| Light anhydrous silicic acid | 0.3 | 0.3 | 0.3 | 0.3 |
| Magnesium stearate | 0.5 | 0.5 | 0.5 | 0.5 |
| Total | 100.0 | 100.0 | 100.0 | 100.0 |
| Tablet hardness (daN) | >20 | >20 | 16.2 | 18.9 |
| Disintegration time (min) | 18.2 | 23.6 | 26.8 | 29.7 |
| Degree of abrasion (%) | 0.00 | 0.11 | 0.22 | 5.14 |

The results of the above tests revealed that when tablets of Keishibukuryogan extract powder contain sodium hydrogen carbonate and croscarmellose sodium, the tablets have sufficient hardness and are hardly abraded.

Example 3 and Comparative Examples 3-1 to 3-4

Powder mixtures for tableting were prepared according to formulae shown in the following table 4 and were compressed using a tableting machine to obtain test tablets weighing 540 mg.

Figure 3:
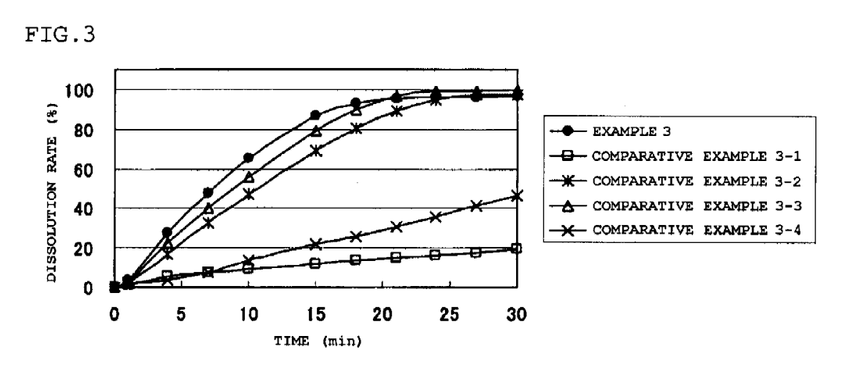
FIG. 3 shows dissolution curves of tablets in Example 3 and Comparative Examples 3-1 to 3-4.

Then, the obtained test tablets were subjected to the disintegration test and the dissolution test as in Example 1. The test results are also shown in the following Table 4. FIG. 3 shows dissolution curves of Example 3 and Comparative Examples 3-1 to 3-4.

TABLE 4

|  |  | Example 3 | Comparative Example 3-1 | Comparative Example 3-2 | Comparative Example 3-3 | Comparative Example 3-4 |
|---|---|---|---|---|---|---|
| Formula (%) | Keishikajutsubuto extract powder | 60.0 | 60.0 | 60.0 | 60.0 | 60.0 |
|  | Sodium hydrogen carbonate | 5.0 | 0.0 | 5.0 | 10.0 | 0.0 |
|  | Croscarmellose sodium | 5.0 | 0.0 | 0.0 | 0.0 | 10.0 |
|  | Crystalline cellulose | 29.2 | 39.2 | 34.2 | 29.2 | 29.2 |
|  | Light anhydrous silicic acid | 0.3 | 0.3 | 0.3 | 0.3 | 0.3 |
|  | Magnesium stearate | 0.5 | 0.5 | 0.5 | 0.5 | 0.5 |
|  | Total | 100.0 | 100.0 | 100.0 | 100.0 | 100.0 |
| Disintegration time (min) |  | 17 | 62 | 27 | 21 | 33 |
| Dissolution rate | 5 min (%) | 34 | 6 | 22 | 28 | 5 |
|  | 10 min (%) | 65 | 10 | 47 | 56 | 14 |
|  | 15 min (%) | 87 | 12 | 69 | 79 | 22 |
|  | 30 min (%) | 97 | 19 | 97 | 100 | 47 |

The results of the above tests revealed that tablets containing a Keishikajutsubuto extract powder can have a short disintegration time and satisfactory dissolution properties by blending a combination of sodium hydrogen carbonate and croscarmellose sodium.

Example 4 and Comparative Examples 4-1 to 4-3

Powder mixtures for tableting were prepared according to formulae shown in the following table 5 and were compressed using a tableting machine to obtain test tablets weighing 540 mg.

Figure 4:
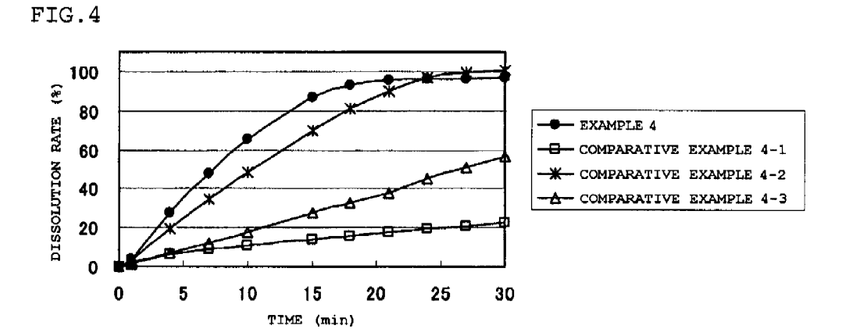
FIG. 4 shows dissolution curves of tablets in Example 4 and Comparative Examples 4-1 to 4-3.

Then, the obtained test tablets were subjected to the disintegration test and the dissolution test as in Example 1. The test results are also shown in the following Table 5. FIG. 4 shows dissolution curves of Example 4 and Comparative Examples 4-1 to 4-3.

TABLE 5

|  |  | Example 4 | Comparative Example 4-1 | Comparative Example 4-2 | Comparative Example 4-3 |
|---|---|---|---|---|---|
| Formula (%) | Juzentaihoto extract powder | 60.0 | 60.0 | 60.0 | 60.0 |
|  | Sodium hydrogen carbonate | 10.0 | 0.0 | 10.0 | 0.0 |
|  | Croscarmellose sodium | 10.0 | 0.0 | 0.0 | 10.0 |
|  | Crystalline cellulose | 19.2 | 39.2 | 29.2 | 29.2 |

TABLE 5-continued

|  | Example 4 | Comparative Example 4-1 | Comparative Example 4-2 | Comparative Example 4-3 |
|---|---|---|---|---|
| Light anhydrous silicic acid | 0.3 | 0.3 | 0.3 | 0.3 |
| Magnesium stearate | 0.5 | 0.5 | 0.5 | 0.5 |
| Total | 100.0 | 100.0 | 100.0 | 100.0 |
| Disintegration time (min) | 18 | 64 | 24 | 39 |
| Dissolution rate 5 min (%) | 34 | 7 | 24 | 9 |
| 10 min (%) | 64 | 11 | 49 | 18 |
| 15 min (%) | 85 | 14 | 70 | 28 |
| 30 min (%) | 103 | 23 | 101 | 57 |

The results of the above tests revealed that tablets containing a Juzentaihoto extract powder can have a short disintegration time and satisfactory dissolution properties by blending a combination of sodium hydrogen carbonate and croscarmellose sodium.

Example 5 and Comparative Examples 5-1 to 5-3

Powder mixtures for tableting were prepared according to formulae shown in the following table 6 and were compressed using a tableting machine to obtain test tablets weighing 540 mg.

Figure 5:
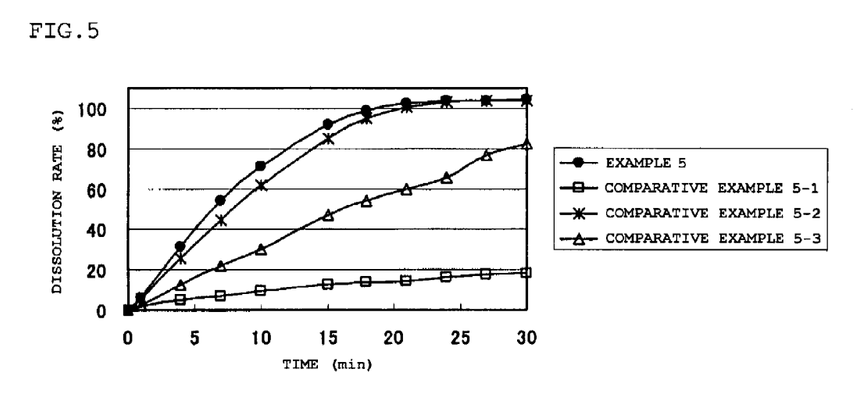
FIG. 5 shows dissolution curves of tablets in Example 5 and Comparative Examples 5-1 to 5-3.

Then, the obtained test tablets were subjected to the disintegration test and the dissolution test as in Example 1. The test results are also shown in the following Table 6. FIG. 5 shows dissolution curves of Example 5 and Comparative Examples 5-1 to 5-3.

TABLE 6

|  |  | Example 5 | Comparative Example 5-1 | Comparative Example 5-2 | Comparative Example 5-3 |
|---|---|---|---|---|---|
| Formula (%) | Sokeikakketsuto extract powder | 60.0 | 60.0 | 60.0 | 60.0 |
|  | Sodium hydrogen carbonate | 10.0 | 0.0 | 10.0 | 0.0 |
|  | Croscarmellose sodium | 10.0 | 0.0 | 0.0 | 10.0 |
|  | Crystalline cellulose | 19.2 | 39.2 | 29.2 | 29.2 |
|  | Light anhydrous silicic acid | 0.3 | 0.3 | 0.3 | 0.3 |
|  | Magnesium stearate | 0.5 | 0.5 | 0.5 | 0.5 |
|  | Total | 100.0 | 100.0 | 100.0 | 100.0 |
| Disintegration time (min) |  | 13 | 60 | 21 | 29 |
| Dissolution rate | 5 min (%) | 39 | 6 | 32 | 16 |
|  | 10 min (%) | 71 | 9 | 62 | 30 |
|  | 15 min (%) | 92 | 12 | 85 | 47 |
|  | 30 min (%) | 104 | 18 | 104 | 82 |

The results of the above tests revealed that tablets containing a Sokeikakketsuto extract powder can have a short disintegration time and satisfactory dissolution properties by blending a combination of sodium hydrogen carbonate and croscarmellose sodium.

Example 6 and Comparative Examples 6-1 to 6-3

Powder mixtures for tableting were prepared according to formulae shown in the following table 7 and were compressed using a tableting machine to obtain test tablets weighing 540 mg.

Figure 6:
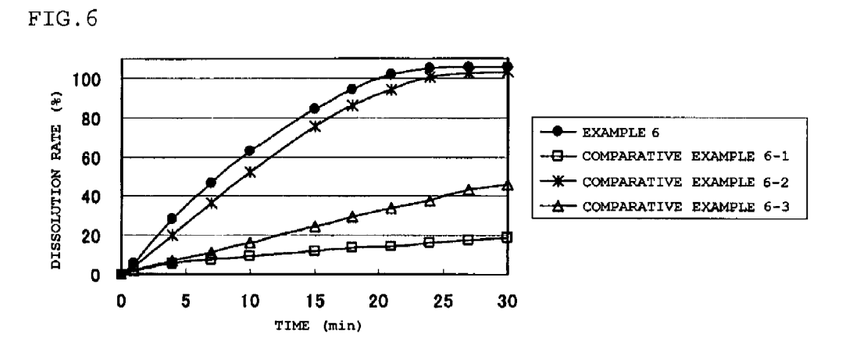
FIG. 6 shows dissolution curves of tablets in Example 6 and Comparative Examples 6-1 to 6-3.

Then, the obtained test tablets were subjected to the disintegration test and the dissolution test as in Example 1. The test results are also shown in the following Table 7. FIG. 6 shows dissolution curves of Example 6 and Comparative Examples 6-1 to 6-3.

TABLE 7

|  |  | Example 6 | Comparative Example 6-1 | Comparative Example 6-2 | Comparative Example 6-3 |
|---|---|---|---|---|---|
| Formula (%) | Yokukansan extract powder | 60.0 | 60.0 | 60.0 | 60.0 |
|  | Sodium hydrogen carbonate | 10.0 | 0.0 | 10.0 | 0.0 |
|  | Croscarmellose sodium | 10.0 | 0.0 | 0.0 | 10.0 |
|  | Crystalline cellulose | 19.2 | 39.2 | 29.2 | 29.2 |
|  | Light anhydrous silicic acid | 0.3 | 0.3 | 0.3 | 0.3 |
|  | Magnesium stearate | 0.5 | 0.5 | 0.5 | 0.5 |
|  | Total | 100.0 | 100.0 | 100.0 | 100.0 |
| Disintegration time (min) |  | 15 | 60 | 23 | 35 |

TABLE 7-continued

|  |  | Example 6 | Comparative Example 6-1 | Comparative Example 6-2 | Comparative Example 6-3 |
|---|---|---|---|---|---|
| Dissolution rate | 5 min (%) | 34 | 6 | 25 | 8 |
|  | 10 min (%) | 63 | 10 | 52 | 17 |
|  | 15 min (%) | 84 | 12 | 75 | 24 |
|  | 30 min (%) | 106 | 19 | 103 | 46 |

The results of the above tests revealed that tablets containing a Yokukansan extract powder can have a short disintegration time and satisfactory dissolution properties by blending a combination of sodium hydrogen carbonate and croscarmellose sodium.

Example 7 and Comparative Examples 7-1 to 7-3

Powder mixtures for tableting were prepared according to formulae shown in the following table 8 and were compressed using a tableting machine to obtain test tablets weighing 540 mg.

Figure 7:
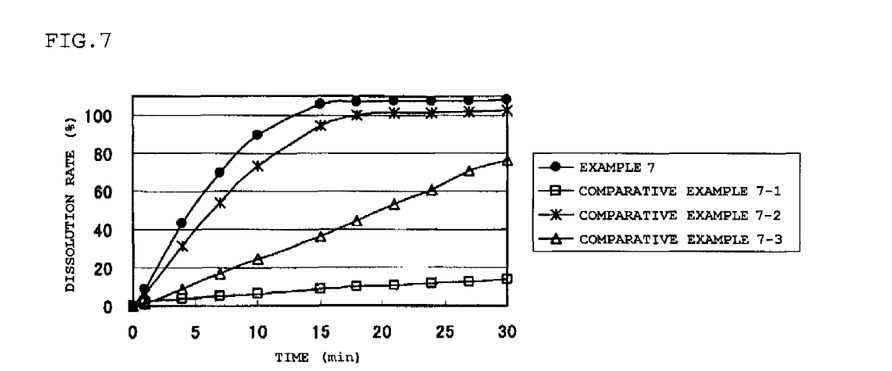
FIG. 7 shows dissolution curves of tablets in Example 7 and Comparative Examples 7-1 to 7-3.

Then, the obtained test tablets were subjected to the disintegration test and the dissolution test as in Example 1. The test results are also shown in the following Table 8. FIG. 7 shows dissolution curves of Example 7 and Comparative Examples 7-1 to 7-3.

TABLE 8

|  |  | Example 7 | Comparative Example 7-1 | Comparative Example 7-2 | Comparative Example 7-3 |
|---|---|---|---|---|---|
| Formula (%) | Eppikajutsuto extract powder | 60.0 | 60.0 | 60.0 | 60.0 |
|  | Sodium hydrogen carbonate | 10.0 | 0.0 | 10.0 | 0.0 |
|  | Croscarmellose sodium | 10.0 | 0.0 | 0.0 | 10.0 |
|  | Crystalline cellulose | 19.2 | 39.2 | 29.2 | 29.2 |
|  | Light anhydrous silicic acid | 0.3 | 0.3 | 0.3 | 0.3 |
|  | Magnesium stearate | 0.5 | 0.5 | 0.5 | 0.5 |
|  | Total | 100.0 | 100.0 | 100.0 | 100.0 |
|  | Disintegration time (min) | 7 | 48 | 14 | 29 |
| Dissolution rate | 5 min (%) | 52 | 4 | 39 | 11 |
|  | 10 min (%) | 90 | 7 | 73 | 24 |
|  | 15 min (%) | 105 | 9 | 95 | 36 |
|  | 30 min (%) | 108 | 14 | 102 | 76 |

The results of the above tests revealed that tablets containing an Eppikajutsuto extract powder can have a short disintegration time and satisfactory dissolution properties by blending a combination of sodium hydrogen carbonate and croscarmellose sodium.

Examples 8 and 9 and Comparative Examples 8-1 and 9-1

Powder mixtures for tableting were prepared according to formulae shown in the following table 9 and were compressed using a tableting machine to obtain test tablets weighing 540 mg.

Figure 8:
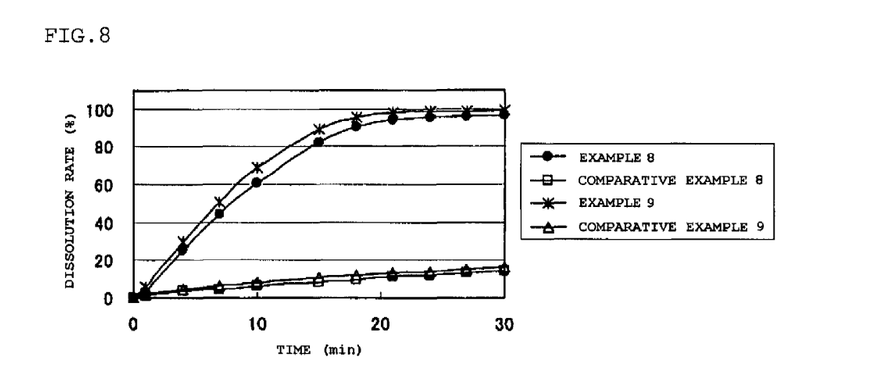
FIG. 8 shows dissolution curves of tablets in Examples 8 and 9 and Comparative Examples 8 and 9.

Then, the obtained test tablets were subjected to the disintegration test and the dissolution test as in Example 1. The test results are also shown in the following Table 9. FIG. 8 shows dissolution curves of Examples 8 and 9 and Comparative Examples 8 and 9.

TABLE 9

|  |  | Example 8 | Comparative Example 8 | Example 9 | Comparative Example 9 |
|---|---|---|---|---|---|
| Formula (%) | Goreisan extract powder | 60.0 | 60.0 | — | — |
|  | Maoto extract powder | — | — | 60.0 | 60.0 |
|  | Sodium hydrogen carbonate | 5.0 | 0.0 | 5.0 | 0.0 |
|  | Croscarmellose sodium | 5.0 | 0.0 | 5.0 | 0.0 |
|  | Crystalline cellulose | 29.2 | 39.2 | 29.2 | 29.2 |
|  | Light anhydrous silicic acid | 0.3 | 0.3 | 0.3 | 0.3 |
|  | Magnesium stearate | 0.5 | 0.5 | 0.5 | 0.5 |
|  | Total | 100.0 | 100.0 | 100.0 | 90.0 |
|  | Disintegration time (min) | 19 | 79 | 14 | 75 |
| Dissolution rate | 5 min (%) | 32 | 4 | 37 | 5 |
|  | 10 min (%) | 61 | 6 | 69 | 8 |
|  | 15 min (%) | 82 | 8 | 89 | 11 |
|  | 30 min (%) | 97 | 15 | 96 | 16 |

The results of the above tests revealed that tablets containing Goreisan extract powder and Maoto extract powder can have a short disintegration time and satisfactory dissolution properties by blending a combination of sodium hydrogen carbonate and croscarmellose sodium.

Examples 10 to 21 and Comparative Examples 10 to 21

Powder mixtures for tableting were prepared according to formulae shown in the following tables 10 to 13 and were compressed using a tableting machine to obtain test tablets weighing 540 mg.

Then, the obtained test tablets were subjected to the disintegration test as in Example 1. The test results are also shown in the following Tables 10 to 13.

TABLE 10

| | | | Example 10 | Example 11 | Example 12 | Example 13 | Example 14 | Example 15 |
|---|---|---|---|---|---|---|---|---|
| Formula (%) | Extract powder | Kakkonto | 60.0 | — | — | — | — | — |
| | | Shoseiryuto | — | 60.0 | — | — | — | — |
| | | Tokishakuyakusan | — | — | 60.0 | — | — | — |
| | | Kamishoyosan | — | — | — | 60.0 | — | — |
| | | Shakuyakukanzoto | — | — | — | — | 60.0 | — |
| | | Goshajinkigan | — | — | — | — | — | 60.0 |
| | | Kakkontokasenkyushin'i | — | — | — | — | — | — |
| | | Keishininjinto | — | — | — | — | — | — |
| | | Maobushisaishinto | — | — | — | — | — | — |
| | | Hochuekkito | — | — | — | — | — | — |
| | | Tokakujokito | — | — | — | — | — | — |
| | | Bofutushosan | — | — | — | — | — | — |
| | Sodium hydrogen carbonate | | 10.0 | 10.0 | 10.0 | 10.0 | 10.0 | 10.0 |
| | Croscarmellose sodium | | 10.0 | 10.0 | 10.0 | 10.0 | 10.0 | 10.0 |
| | Crystalline cellulose | | 19.2 | 19.2 | 19.2 | 19.2 | 19.2 | 19.2 |
| | Light anhydrous silicic acid | | 0.3 | 0.3 | 0.3 | 0.3 | 0.3 | 0.3 |
| | Magnesium stearate | | 0.5 | 0.5 | 0.5 | 0.5 | 0.5 | 0.5 |
| | Total | | 100.0 | 100.0 | 100.0 | 100.0 | 100.0 | 100.0 |
| Disintegration time (min) | | | 25 | 15 | 22 | 20 | 21 | 23 |

TABLE 11

| | | | Example 16 | Example 17 | Example 18 | Example 19 | Example 20 | Example 21 |
|---|---|---|---|---|---|---|---|---|
| Formula (%) | Extract powder | Kakkonto | — | — | — | — | — | — |
| | | Shoseiryuto | — | — | — | — | — | — |
| | | Tokishakuyakusan | — | — | — | — | — | — |
| | | Kamishoyosan | — | — | — | — | — | — |
| | | Shakuyakukanzoto | — | — | — | — | — | — |
| | | Goshajinkigan | — | — | — | — | — | — |
| | | Kakkontokasenkyushin'i | 60.0 | — | — | — | — | — |
| | | Keishininjinto | — | 60.0 | — | — | — | — |
| | | Maobushisaishinto | — | — | 60.0 | — | — | — |
| | | Hochuekkito | — | — | — | 60.0 | — | — |
| | | Tokakujokito | — | — | — | — | 60.0 | — |
| | | Bofutushosan | — | — | — | — | — | 60.0 |
| | Sodium hydrogen carbonate | | 10.0 | 10.0 | 10.0 | 10.0 | 10.0 | 10.0 |
| | Croscarmellose sodium | | 10.0 | 10.0 | 10.0 | 10.0 | 10.0 | 10.0 |
| | Crystalline cellulose | | 19.2 | 19.2 | 19.2 | 19.2 | 19.2 | 19.2 |
| | Light anhydrous silicic acid | | 0.3 | 0.3 | 0.3 | 0.3 | 0.3 | 0.3 |
| | Magnesium stearate | | 0.5 | 0.5 | 0.5 | 0.5 | 0.5 | 0.5 |
| | Total | | 100.0 | 100.0 | 100.0 | 100.0 | 100.0 | 100.0 |
| Disintegration time (min) | | | 20 | 21 | 24 | 16 | 13 | 12 |

TABLE 12

| | | | Comparative Example 10 | Comparative Example 11 | Comparative Example 12 | Comparative Example 13 | Comparative Example 14 | Comparative Example 15 |
|---|---|---|---|---|---|---|---|---|
| Formula (%) | Extract powder | Kakkonto | 60.0 | — | — | — | — | — |
| | | Shoseiryuto | — | 60.0 | — | — | — | — |
| | | Tokishakuyakusan | — | — | 60.0 | — | — | — |
| | | Kamishoyosan | — | — | — | 60.0 | — | — |
| | | Shakuyakukanzoto | — | — | — | — | 60.0 | — |
| | | Goshajinkigan | — | — | — | — | — | 60.0 |

TABLE 12-continued

|  | Comparative Example 10 | Comparative Example 11 | Comparative Example 12 | Comparative Example 13 | Comparative Example 14 | Comparative Example 15 |
|---|---|---|---|---|---|---|
| kakkontokasenkyushin'i | — | — | — | — | — | — |
| Keishininjinto | — | — | — | — | — | — |
| Maobushisaishinto | — | — | — | — | — | — |
| Hochuekkito | — | — | — | — | — | — |
| Tokakujokito | — | — | — | — | — | — |
| Bofutushosan | — | — | — | — | — | — |
| Sodium hydrogen carbonate | 0.0 | 0.0 | 0.0 | 0.0 | 0.0 | 0.0 |
| Croscarmellose sodium | 0.0 | 0.0 | 0.0 | 0.0 | 0.0 | 0.0 |
| Crystalline cellulose | 39.2 | 39.2 | 39.2 | 39.2 | 39.2 | 39.2 |
| Light anhydrous silicic acid | 0.3 | 0.3 | 0.3 | 0.3 | 0.3 | 0.3 |
| Magnesium stearate | 0.5 | 0.5 | 0.5 | 0.5 | 0.5 | 0.5 |
| Total | 100.0 | 100.0 | 100.0 | 100.0 | 100.0 | 100.0 |
| Disintegration time (min) | >60 | >60 | >60 | >60 | >60 | >60 |

TABLE 13

|  |  |  | Comparative Example 16 | Comparative Example 17 | Comparative Example 18 | Comparative Example 19 | Comparative Example 20 | Comparative Example 21 |
|---|---|---|---|---|---|---|---|---|
| Formula (%) | Extract powder | Kakkonto | — | — | — | — | — | — |
|  |  | Shoseiryuto | — | — | — | — | — | — |
|  |  | Tokishakuyakusan | — | — | — | — | — | — |
|  |  | Kamishoyosan | — | — | — | — | — | — |
|  |  | Shakuyakukanzoto | — | — | — | — | — | — |
|  |  | Goshajinkigan | — | — | — | — | — | — |
|  |  | Kakkontokasenkyushin'i | 60.0 | — | — | — | — | — |
|  |  | Keishininjinto | — | 60.0 | — | — | — | — |
|  |  | Maobushisaishinto | — | — | 60.0 | — | — | — |
|  |  | Hochuekkito | — | — | — | 60.0 | — | — |
|  |  | Tokakujokito | — | — | — | — | 60.0 | — |
|  |  | Bofutushosan | — | — | — | — | — | 60.0 |
|  | Sodium hydrogen carbonate |  | 0.0 | 0.0 | 0.0 | 0.0 | 0.0 | 0.0 |
|  | Croscarmellose sodium |  | 0.0 | 0.0 | 0.0 | 0.0 | 0.0 | 0.0 |
|  | Crystalline cellulose |  | 39.2 | 39.2 | 39.2 | 39.2 | 39.2 | 39.2 |
|  | Light anhydrous silicic acid |  | 0.3 | 0.3 | 0.3 | 0.3 | 0.3 | 0.3 |
|  | Magnesium stearate |  | 0.5 | 0.5 | 0.5 | 0.5 | 0.5 | 0.5 |
|  | Total |  | 100.0 | 100.0 | 100.0 | 100.0 | 100.0 | 100.0 |
|  | Disintegration time (min) |  | >60 | >60 | >60 | >60 | >60 | 47 |

The results of the above tests revealed that tablets containing any extract powder of the kakkonto extract powder, the Shoseiryuto extract powder, the Tokishakuyakusan extract powder, the Kamishoyosan extract powder, the Shakuyakukanzoto extract powder, the Goshajinkigan extract powder, the Kakkontokasenkyushin'i extract powder, the Keishininjinto extract powder, the Maobushisaishinto extract powder, the Hochuekkito extract powder, the Tokakujokito extract powder, or the Bofutushosan extract powder can have a short disintegration time by blending a combination of sodium hydrogen carbonate and croscarmellose sodium.

Examples 22 to 33

Powder mixtures for tableting were prepared according to formulae shown in the following tables 14 to 16 and were compressed using a tableting machine to obtain test tablets weighing 540 mg.

Then, the obtained test tablets were subjected to the disintegration test as in Example 1. The test results are also shown in the following Tables 14 to 16.

TABLE 14

|  | Example 22 | Example 23 | Example 24 | Example 25 |
|---|---|---|---|---|
| Keishibukuryogan extract powder | 60.0 | 60.0 | 60.0 | 60.0 |
| Sodium hydrogen carbonate | 5.0 | 5.0 | 5.0 | 5.0 |
| Croscarmellose sodium | 5.0 | 5.0 | 5.0 | 5.0 |
| Light anhydrous silicic acid | 0.3 | 0.3 | 0.3 | 0.3 |
| Magnesium stearate | 0.5 | 0.5 | 0.5 | 0.5 |
| Crystalline cellulose | 29.2 | — | — | — |
| Dextrin | — | 29.2 | — | — |

TABLE 14-continued

|  | Example 22 | Example 23 | Example 24 | Example 25 |
|---|---|---|---|---|
| Calcium hydrogen phosphate | — | — | 29.2 | — |
| Lactose | — | — | — | 29.2 |
| Total | 100.0 | 100.0 | 100.0 | 100.0 |
| Disintegration time (min) | 13 | 22 | 19 | 21 |
| Dissolution rate 5 min (%) | 45 | 29 | 41 | 34 |
| 10 min (%) | 82 | 58 | 73 | 64 |
| 15 min (%) | 98 | 78 | 89 | 85 |
| 30 min (%) | 101 | 99 | 99 | 99 |

TABLE 15

|  | Example 26 | Example 27 | Example 28 | Example 29 |
|---|---|---|---|---|
| Keishikajutsubuto extract powder | 60.0 | 60.0 | 60.0 | 60.0 |
| Sodium hydrogen carbonate | 5.0 | 5.0 | 5.0 | 5.0 |
| Croscarmellose sodium | 5.0 | 5.0 | 5.0 | 5.0 |
| Light anhydrous silicic acid | 0.3 | 0.3 | 0.3 | 0.3 |
| Magnesium stearate | 0.5 | 0.5 | 0.5 | 0.5 |
| Crystalline cellulose | 29.2 | — | — | — |
| Dextrin | — | 29.2 | — | — |
| Calcium hydrogen phosphate | — | — | 29.2 | — |
| Lactose | — | — | — | 29.2 |
| Total | 100.0 | 100.0 | 100.0 | 100.0 |
| Disintegration time (min) | 17 | 27 | 19 | 28 |
| Dissolution rate 5 min (%) | 34 | 19 | 32 | 23 |
| 10 min (%) | 65 | 42 | 59 | 45 |
| 15 min (%) | 87 | 60 | 77 | 64 |
| 30 min (%) | 97 | 94 | 98 | 97 |

TABLE 16

|  | Example 30 | Example 31 | Example 32 | Example 33 |
|---|---|---|---|---|
| Juzentaihoto extract powder | 60.0 | 60.0 | 60.0 | 60.0 |
| Sodium hydrogen carbonate | 10.0 | 10.0 | 10.0 | 10.0 |
| Croscarmellose sodium | 10.0 | 10.0 | 10.0 | 10.0 |
| Light anhydrous silicic acid | 0.3 | 0.3 | 0.3 | 0.3 |
| Magnesium stearate | 0.5 | 0.5 | 0.5 | 0.5 |
| Crystalline cellulose | 19.2 | — | — | — |
| Dextrin | — | 19.2 | — | — |
| Calcium hydrogen phosphate | — | — | 19.2 | — |
| Lactose | — | — | — | 19.2 |
| Total | 100.0 | 100.0 | 100.0 | 100.0 |
| Disintegration time (min) | 18 | 24 | 16 | 23 |
| Dissolution rate 5 min (%) | 34 | 29 | 33 | 30 |
| 10 min (%) | 64 | 57 | 64 | 57 |
| 15 min (%) | 85 | 77 | 84 | 77 |
| 30 min (%) | 103 | 99 | 97 | 99 |

The results of the above test revealed that tablets can have a short disintegration time by blending a combination of sodium hydrogen carbonate and croscarmellose sodium.

The invention claimed is:

1. A tablet composition containing Kampo extract comprising a Kampo extract powder, croscarmellose sodium, and sodium hydrogen carbonate,
    wherein the amount of the croscarmellose sodium is 8 to 20 parts by weight based on 100 parts by weight of the Kampo extract powder,
    wherein a disintegration time of the tablet composition is 19 minutes or less, and
    wherein the Kampo extract powder is at least one extract powder selected from the group consisting of Keishikajutsubuto, Juzentaihoto, Sokeikakketsuto, Tokakujokito, Yokukansan and Goreisan.

2. The tablet composition containing Kampo extract according to claim 1, wherein the amount of the croscarmellose sodium is 10 to 20 parts by weight based on 100 parts by weight of the Kampo extract powder.

3. The tablet composition containing Kampo extract according to claim 1, wherein the amount of the sodium hydrogen carbonate is 5 to 30 parts by weight based on 100 parts by weight of the Kampo extract powder.

4. The tablet composition containing Kampo extract according to claim 1, wherein the Kampo extract powder is Yokukansan.

5. The tablet composition containing Kampo extract according to claim 1, wherein the amount of the sodium hydrogen carbonate is 8 to 20 parts by weight based on 100 parts by weight of the Kampo extract powder.

6. A tablet composition containing Kampo extract consisting essentially of a Kampo extract powder, croscarmellose sodium, and sodium hydrogen carbonate,
- wherein the amount of the croscarmellose sodium is 8 to 20 parts by weight based on 100 parts by weight of the Kampo extract powder,
- wherein a disintegration time of the tablet composition is 19 minutes or less, and
- wherein the Kampo extract powder is at least one extract powder selected from the group consisting of Keishikajutsubuto, Juzentaihoto, Sokeikakketsuto, Tokakujokito, Yokukansan and Goreisan.

7. A tablet composition containing Kampo extract consisting essentially of a Kampo extract powder, croscarmellose sodium, sodium hydrogen carbonate, and one or more excipient(s) selected from a group consisting of diluents, binder, fluidizer and lubricant,
- wherein the amount of the croscarmellose sodium is 8 to 20 parts by weight based on 100 parts by weight of the Kampo extract powder,
- wherein a disintegration time of the tablet composition is 19 minutes or less, and
- wherein the Kampo extract powder is at least one extract powder selected from the group consisting of Keishikajutsubuto, Juzentaihoto, Sokeikakketsuto, Tokakujokito, Yokukansan and Goreisan.

8. A tablet composition containing Kampo extract consisting essentially of a Kampo extract powder, croscarmellose sodium, sodium hydrogen carbonate, and one or more excipient(s) selected from a group consisting of sugar, sugar alcohol, starch, maize starch, dextrin, pregelatinized starches, crystalline cellulose, hydroxypropyl cellulose, inorganic substances and fatty acid,
- wherein the amount of the croscarmellose sodium is 8 to 20 parts by weight based on 100 parts by weight of the Kampo extract powder,
- wherein a disintegration time of the tablet composition is 19 minutes or less, and
- wherein the Kampo extract powder is at least one extract powder selected from the group consisting of Keishikajutsubuto, Juzentaihoto, Sokeikakketsuto, Tokakujokito, Yokukansan and Goreisan.

9. A tablet composition containing Kampo extract consisting essentially of a Kampo extract powder, croscarmellose sodium, sodium hydrogen carbonate, and one or more excipient(s) selected from a group consisting of lactose, cornstarch, maltose, mannitol, maize starch, dextrin, pregelatinized starch, crystalline cellulose hydroxypropyl cellulose, synthetic aluminum silicate, calcium phosphate, calcium hydrogen phosphate, talc, light anhydrous silicic acid, magnesium stearate and calcium stearate,
- wherein the amount of the croscarmellose sodium is 8 to 20 parts by weight based on 100 parts by weight of the Kampo extract powder,
- wherein a disintegration time of the tablet composition is 19 minutes or less, and
- wherein the Kampo extract powder is at least one extract powder selected from the group consisting of Keishikajutsubuto, Juzentaihoto, Sokeikakketsuto, Tokakujokito, Yokukansan and Goreisan.

\* \* \* \* \*